United States Patent
Yang et al.

(10) Patent No.: US 9,920,008 B2
(45) Date of Patent: Mar. 20, 2018

(54) CATALYST FOR SYNTHESIZING ETHYLENIMINE AS WELL AS PREPARATION METHOD AND APPLICATION THEREOF

(71) Applicant: XI'AN MODERN CHEMISTRY RESEARCH INSTITUTE, Xi'an, Shaanxi (CN)

(72) Inventors: Jianming Yang, Shaanxi (CN); Jian Lu, Shaanxi (CN); Suning Mei, Shaanxi (CN); Qinwei Yu, Shaanxi (CN); Feng Hui, Shaanxi (CN); Yani Li, Shaanxi (CN); Fengwei Zhao, Shaanxi (CN); Weiqiang Wang, Shaanxi (CN); Wei Wang, Shaanxi (CN)

(73) Assignee: XI'AN MODERN CHEMISTRY RESEARCH INSTITUTE, Xi'An, Shaanxi (CN)

( * ) Notice: Subject to any disclaimer, the term of this patent is extended or adjusted under 35 U.S.C. 154(b) by 0 days.

(21) Appl. No.: 15/105,499

(22) PCT Filed: Sep. 5, 2014

(86) PCT No.: PCT/CN2014/086008
§ 371 (c)(1),
(2) Date: Jun. 16, 2016

(87) PCT Pub. No.: WO2015/090084
PCT Pub. Date: Jun. 25, 2015

(65) Prior Publication Data
US 2016/0318863 A1 Nov. 3, 2016

(30) Foreign Application Priority Data
Dec. 18, 2013 (CN) .......................... 2013 1 0698874

(51) Int. Cl.
```
C07D 203/08    (2006.01)
B01J 27/182    (2006.01)
B01J 37/04     (2006.01)
B01J 37/08     (2006.01)
B01J 37/26     (2006.01)
B01J 37/28     (2006.01)
B01J 21/06     (2006.01)
B01J 21/08     (2006.01)
B01J 23/78     (2006.01)
B01J 37/00     (2006.01)
B01J 35/00     (2006.01)
B01J 35/10     (2006.01)
B01J 37/02     (2006.01)
```

(52) U.S. Cl.
CPC .......... *C07D 203/08* (2013.01); *B01J 21/063* (2013.01); *B01J 21/08* (2013.01); *B01J 23/78* (2013.01); *B01J 27/182* (2013.01); *B01J 35/0006* (2013.01); *B01J 35/1014* (2013.01); *B01J 35/1038* (2013.01); *B01J 35/1061* (2013.01); *B01J 37/0009* (2013.01); *B01J 37/0018* (2013.01); *B01J 37/0217* (2013.01); *B01J 37/04* (2013.01); *B01J 37/082* (2013.01); *B01J 37/088* (2013.01); *B01J 37/26* (2013.01); *B01J 37/28* (2013.01)

(58) Field of Classification Search
CPC .................................................. C07D 203/08
See application file for complete search history.

(56) References Cited

U.S. PATENT DOCUMENTS

| | | | |
|---|---|---|---|
| 4,977,118 A | 12/1990 | Tsuneki et al. | |
| 5,231,189 A | 7/1993 | Tuneki et al. | |
| 5,236,107 A | 8/1993 | Shimasaki et al. | |
| 5,262,570 A | 11/1993 | Shimasaki et al. | |
| 2009/0280298 A1* | 11/2009 | Rosenzweig | C23C 30/00 428/156 |
| 2011/0237820 A1* | 9/2011 | Besecker | B01J 23/002 558/321 |

FOREIGN PATENT DOCUMENTS

| CN | 1043316 A | 9/1999 |
|---|---|---|
| CN | 103816927 A | 5/2014 |

OTHER PUBLICATIONS

International Search Report in connection with PCT International Application No. PCT/CN2014/086008.

* cited by examiner

*Primary Examiner* — Shawquia Jackson
(74) *Attorney, Agent, or Firm* — John P. White; Cooper & Dunham LLP

(57) ABSTRACT

The present invention relates to a catalyst for synthesizing ethylenimine as well as a preparation method and application thereof. The related catalyst comprises a carrier and metal ions loaded on the carrier; the carrier is a composite oxide comprising titanium, silicon and phosphorus elements; the metal ions are magnesium ions, iron ions and cesium ions; the molar ratio of the magnesium ions to the iron ions to the cesium ions is (1-10):1:0.1; the mass of all metal ions is 0.5-10 percent of that of the carrier. In the related preparation method, a catalyst precursor is roasted at the temperature of 350-650° C., so that the catalyst is obtained; the catalyst precursor is the mixture of the carrier, soluble salt of magnesium, soluble salt of iron and soluble salt of cesium. The present invention also provides the application of the catalyst to synthesis of the ethylenimine by using amino alcohol as the raw material. Compared with a common catalyst which has the requirement on the temperature of over 400° C., the catalyst of the present invention obviously reduces the reaction temperature. The prepared catalyst can catalyze the intramolecular dehydration reaction of the amino alcohol and has relatively excellent selectivity.

12 Claims, No Drawings

US 9,920,008 B2

CATALYST FOR SYNTHESIZING ETHYLENIMINE AS WELL AS PREPARATION METHOD AND APPLICATION THEREOF

TECHNICAL FIELD

The present invention belongs to a field of chemical technology, and particularly relates to a catalyst for synthesizing ethylenimine as well as a preparation method and application thereof.

BACKGROUND

Ethylenimine, also referred to as aziridine, is an important fine chemical product, and has a wide application in the fields of medicine, pesticide, high-energy fuel, bonding agent, and the like.

Initially, ethylenimine is prepared industrially by liquid-phase method using monoethanolamine as a raw material and concentrated sulfuric acid as a dehydrating agent. During this reaction, it is necessary to add a concentrated alkaline, so that the cost is high and the useless by-products of inorganic salts are generated, which causes severe environment pollution.

A catalyst consisting of tungsten oxide and silicon oxide and the application thereof for the synthesis of ethylenimine are disclosed in U.S. Pat. No. 4,301,036.

A method of synthesizing ethylenimine by using a niobium/tantalum oxide and an alkaline earth metal oxide and (or) an iron/chromium oxide as catalysts is disclosed in U.S. Pat. No. 4,488,591. A method of preparing ethylenimine by using the complex oxide of niobium or tantalum oxide and an alkaline earth metal oxide (BaO) as a catalyst is disclosed in U.S. Pat. No. 433717. The method comprises the following steps: preparing the solution to be loaded from niobium halide or tantalum halide; loading the solution on the surface of the carrier (0.1 m$^2$/g–1.0 m$^2$/g), then roasting the loaded carrier at a temperature in a range of 450° C. to 550° C. for 2-4 hours to give the catalyst. The reaction temperature of preparing ethylenimine is 400° C., and the ethanolamine conversion rate is 13.87 (mol) % with a selectivity for ethylenimine of 82.09 (mol) %. In addition, a small amount of acetaldehyde, ethylene amine, pyrazine and alkylpyrazine are also generated.

A catalyst for synthesizing ethylenimine compounds is disclosed in CN2007100109625. The catalyst is $X_a Y_b O_c$ (HZSM-5)$_d$, wherein X is an alkaline metal, Y is phosphorus element or boron element, O is an oxygen element; a, b, c, and d are the molar ratios of the elements X, Y, O, and ZSM-5, respectively; and when d=1, a=0.01-0.1, b=0.001-0.1, and c is dependent on a and b. The reaction temperature of preparing ethylenimine is 420° C., and the ethanolamine conversion rate is 84 (mol) % with a selectivity for ethylenimine of 84 (mol) %.

The specific surface area and the acid-base intensity of a catalyst for ethylenimine are closely related to the activity and selectivity of the catalyst. Generally, the loaded catalyst would have a relatively high catalytic activity only when the specific surface area is relatively high. However, a roast step at a high temperature (≥600° C.) is needed to prepare such a catalyst. The local high temperature resulting from a strong exothermic reaction may significantly decrease the specific surface area of the roasted catalyst, resulting in the decrease in activity and selectivity of the catalyst. In view of the economic factors in the industrial processes, it is generally more important to seek for a catalyst with higher selectivity and longer service life than to improve the conversion rate of the materials, so as to ensure the conversion of the materials into the desired target products as more as possible and reduce the generation of the unwanted by-products.

In the prior art, the intramolecular dehydration reaction of amino alcohols is carried out at a relative low temperature (about 370° C.), and under such a low temperature, the activity and selectivity of the catalyst are relatively low. The reaction is generally carried out quickly at a high reaction temperature, generally above 400° C. However, the deamination and intramolecular condensation reactions of amino alcohols may occur easily at such a high temperature, and thus the by-products are increased, so that the selectivity for ethylenimine is decreased with the weight selectivity of the catalyst being lower than 65 wt %, and the catalyst has a short service life.

SUMMARY OF THE INVENTION

With respect to the defects or deficiencies in the prior art, one objective of the present invention is to provide a catalyst with a large specific surface area, a large pore volume, a good activity at low temperature, and a long service life, for synthesizing ethylenimine. For this purpose, the present invention provides a catalyst comprising a carrier and metal ions loaded on the carrier; the carrier is a composite oxide comprising titanium, silicon and phosphorus elements; the metal ions are magnesium ion, iron ion and cesium ion, the molar ratio of the magnesium ion to the iron ion to the cesium ion is (1-10):1:0.1; and the total mass of all the metal ions is 0.5%-10% of that of the carrier.

Another objective of the present invention is to provide preparation methods of the carrier and the catalyst, respectively.

For this purpose, the present invention provides a method for the preparation of the carrier comprising the following steps:

(1) mixing silicon oxide, titanium oxide, and an ammonium phosphate salt in an amount of the weight ratio of 5-20:80:15-5 in the oxides form of $SiO_2$ to $TiO_2$ to $P_2O_5$; adding a binder thereto, then kneading and extruding the resulting mixture; drying the extruded mixture, then roasting the dried mixture at a temperature in a range of 600-900° C., thereby obtaining a composite oxide comprising titanium, silicon and phosphorus elements;

Wherein the ammonium phosphate salt is ammonium phosphate, diammonium phosphate, or ammonium dihydrogen phosphate; and the binder is silica sol or pseudo-boehmite;

(2) carrying out fluoridation by reacting the resulting composite oxide in the step (1) with hydrogen fluoride in the absence of oxygen at a temperature in a range of 100-200° C. to give a catalyst carrier.

Preferably, the binder is used in an amount of 10%-30% of the mass of the titanium oxide. A method for the preparation of the catalyst provided by the present invention comprises: roasting a catalyst precursor at a temperature in a range of 350-650° C. to give the catalyst; the catalyst precursor is a mixture of the carrier, a soluble salt of magnesium, a soluble salt of iron and a soluble salt of cesium.

With respect to the defects or deficiencies in the prior art, the present invention further provides use of the catalyst for the synthesis of ethylenimine by using amino alcohol as a raw material.

Preferably, when ethylenimine is synthesized by using amino alcohol as a raw material in the present of the above mentioned catalyst, the reaction temperature is in a range of 370-385° C.

The advantages of the present invention compared with the prior art lie in that:

(1) The catalyst for the synthesis of ethylenimine according to the present invention is prepared at the temperature in a range of 100-200° C. by using $SiO_2$ as a pore-forming agent with the use of the characteristics that $SiO_2$ in the carrier has a chain structure and is apt to react with HF to generate a volatile compound silicon fluoride, thus generating a continuous pore structure after $SiO_2$ is removed by fluoridation, thereby increasing the specific surface area and the pore volume of the catalyst. Therefore, the catalyst according to the present application has a high specific surface area and a large pore volume, wherein, the specific surface area of the catalyst is $\geq 40$ m$^2$/g, the pore volume is $\geq 0.20$ ml/g, and the average pore diameter is $\leq 9$ nm. Furthermore, such a catalyst improves the diffusion of the raw material and product in the catalyst pores.

(2) The catalyst for the synthesis of ethylenimine according to the present invention requires a significantly low reaction temperature compared with the synthesis which generally requires a reaction temperature of more than 400° C. The synthesized catalyst according to the present application may catalyze the intramolecular dehydration reaction of amino alcohols and have an optimized selectivity. The monoethanolamine conversion rate at the temperature of 370° C. may be up to 38%, the selectivity to ethylenimine may be up to 95%.

(3) The catalyst according to the present invention has a long service life and a substantially constant activity. The monoethanolamine conversion rate during a time period of 1,000 hours may be up to 32%, and the selectivity to ethylenimine may be up to 96%.

(4) The catalyst according to the present invention may be used in the intramolecular dehydration reaction of various amino alcohols.

BEST MODE FOR CARRYING OUT THE INVENTION

In order to achieve the objectives above, the following technical solutions are adopted according to the present invention:

The catalyst with a high specific surface area and a large pore volume is prepared at the temperature in a range of 100-200° C. by using $SiO_2$ as a pore-forming agent. Utilizing the characteristics that $SiO_2$ in the carrier has a chain structure and is apt to react with HF to generate a volatile compound silicon fluoride, a continuous pore structure is generated after $SiO_2$ is removed by fluoridation, thereby increasing the specific surface area and the pore volume and resulting the catalyst with high specific surface area and big pore volume. Then, the active ingredients are immersed by the immersing step, thereby obtaining the catalyst according to the present invention.

The amount of the binder according to the present invention may be determined depending on the amount of the mixture of the step (1) capable of being extruded. The silica sol used is an aqueous solution in which the content of silicon dioxide is 20%-30% by mass.

According to the present invention, the soluble salt of magnesium is preferably nitrate or chloride of magnesium; the soluble salt of iron is preferably nitrate or chloride of iron; the soluble salt of cesium is preferably nitrate or chloride of cesium.

The evaluation of activity of the catalyst for the synthesis of ethylenimine prepared according to the present invention may be performed a general fixed-bed tubular reactor with a size of 700 mm×Φ40 mm×6 mm. The catalyst is filled into the reactor, heated to the reaction temperature, and fed by a metering pump. After the reaction is completed, sampling and analyzing of the samples are performed on the analyzer GC-930 gas chromatograph.

The ethanolamine conversion rate and the selectivity for ethylenimine according to the present invention are defined as follows:

ethanolamine conversion rate $C_{MEA}$, %=1-(chromatographic area percentage of ethanol amine in product solution)

selectivity for product S, %=(chromatographic area percentage of ethylenimine in product solution)/ (chromatographic area percentage of other components except for ethanol amine in product solution)

The catalyst for the synthesis of ethylenimine according to the present invention may further be used in the intramolecular dehydration reaction of additional amino alcohols. The amino alcohol is an amino alcohol compound with an ortho structure, specifically the amino alcohol has the following structure:

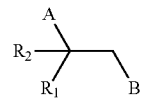

Wherein, $R_1$ is hydrogen, methyl, ethyl, or hydroxymethyl; $R_2$ is hydrogen, methyl, ethyl, or hydroxymethyl; A is hydroxyl or amino, B is hydroxyl or amino, but A and B are not hydroxyl or amino simultaneously. The amino alcohols are ethanolamine, isopropanolamine, 3-amino-1,2-propanediol, 2-amino-2-methyl-1-propanol, as well as other aminobutanol and aminopentanol. Preferably, the amino alcohols are 3-amino-1,2-propanediol and 2-amino-2-methyl-1-propanol.

The present invention will be further explained and described below with reference to the following preferable examples provided by the inventor, but is not limited thereto.

EXAMPLE 1

The reactants are stoichiometrically provided in the forms of oxides, viz. silicon oxide, titanium oxide, and an ammonium phosphate salt, with the weight ratio of 5:80:15 of $SiO_2$ to $TiO_2$ to $P_2O_5$.

10 g of white carbon black was mixed with 160 g of titanium dioxide and 55.7 g of diammonium hydrogen phosphate uniformly. Silica sol was added into the mixture in the amount of 20% of the mass of titanium dioxide. The resulting mixture was kneaded and extruded in the form of strip, then dried at 120° C. for 6 hours, roasted at 350° C. for 6 hours in a muffle, and further roasted for 6 hours with the heating rate of 1° C./min until the temperature of 650° C. Thus the composite oxide comprising titanium, silicon and phosphorus elements was obtained.

The composite oxide comprising titanium, silicon and phosphorus elements was cooled and put into the tubular reactor, heated to the temperature of 150° C., then fluoridized for 2 hours with the mixture of HF and $N_2$ in the volume ratio of HF:$N_2$=1:5 to obtain the catalyst carrier. The catalyst carrier, measured by the low-temperature nitrogen adsorption method, has a specific surface area of 42 m²/g, a pore volume of 0.22 ml/g, and an average pore diameter of 5.6 nm.

The solution of 29.6 g of magnesium nitrate, 4.84 g of iron nitrate, and 0.4 g of cesium nitrate was prepared with the load in the molar ratio of magnesium ion to iron ion to cesium ion of 10:1:0.1. After the resulting catalyst carrier was immersed in the solution for 8 hours, it was taken out and dried, then roasted in the air at 450° C. to give the catalyst. The resulting catalyst was filled into the reactor with the filling amount of 30 ml, and heated to the reaction temperature of 370° C. By using nitrogen as the protective gas with the volume ratio of nitrogen to monoethanolamine gas of 16:1 and the total gas space velocity under standard conditions of 3,600 h⁻¹, the reaction was carried out under the condition of normal pressure or vacuum. After the reaction was carried out for 8 hours, the reaction gas was absorbed with water, then sampled and analyzed. The monoethanolamine conversion rate was 38%, and the selectivity to ethylenimine was 95%. After 1,000 hours of reaction, the monoethanolamine conversion rate was 32%, and the selectivity for ethylenimine was 96%.

EXAMPLE 2

The preparation process of the catalyst carrier in Example 2 was the same as that in Example 1, with exception that silicon oxide, titanium oxide, and an ammonium phosphate salt were formulated in the stoichiometric ratio of an amount of the weight ratio of 10:80:10 in the oxides form of $SiO_2$ to $TiO_2$ to $P_2O_5$. The resulting catalyst carrier, measured by the low-temperature nitrogen adsorption method, had a specific surface area of 43.2 m²/g, a pore volume of 0.21 ml/g, and an average pore diameter of 5.8 nm.

The metal ions were loaded in an amount of 5.3% of the mass of the carrier. The solution the soluble metal salts was prepared in the molar ratio of magnesium ion to iron ion to cesium ion of 8:1:0.1. After the resulting catalyst carrier was immersed in the solution for 8 hours, it was taken out and dried, then roasted in the nitrogen at 350° C. to give the catalyst.

The resulting catalyst was filled into the reactor with the filling amount of 30 ml, and heated to the reaction temperature of 380° C. By using nitrogen as the protective gas with the volume ratio of nitrogen to monoethanolamine gas of 16:1 and the total gas space velocity under standard conditions of 3,000 h⁻¹, the reaction was carried out under the condition of normal pressure or vacuum. After the reaction was carried out for 8 hours, the reaction gas was absorbed with water, then sampled and analyzed. The monoethanolamine conversion rate was 68%, and the selectivity for ethylenimine was 96%. After 1,000 hours of reaction, the monoethanolamine conversion rate was 56%, and the selectivity for ethylenimine was 94%.

EXAMPLE 3

The preparation process of the catalyst carrier in Example 2 was the same as that in Example 1, with exception that silicon oxide, titanium oxide, and an ammonium phosphate salt were stoichiometrically formulated in the weight ratio of 15:80:5 in the oxides form of $SiO_2$ to $TiO_2$ to $P_2O_5$. The resulting catalyst carrier, as measured by the low-temperature nitrogen adsorption method, had a specific surface area of 46.8 m²/g, a pore volume of 0.25 ml/g, and an average pore diameter of 6.1 nm.

The metal ions were loaded in an amount of 0.5% of the mass of the carrier. The solution of the soluble metal salts was prepared in the molar ratio of magnesium ion to iron ion to cesium ion of 1:1:0.1. After the resulting catalyst carrier was immersed in the solution for 8 hours, it was taken out and dried, then roasted in the air at 650° C. to give the catalyst. The resulting catalyst was filled into the reactor with the filling amount of 30 ml, and heated to the reaction temperature of 380° C. By using nitrogen as the protective gas with the volume ratio of nitrogen to monoethanolamine gas of 16:1 and the total gas space velocity under standard conditions of 3,200 h⁻¹, the reaction was carried out under the condition of normal pressure or vacuum. After the reaction was carried out for 8 hours, the reaction gas was absorbed with water, then sampled and analyzed. The monoethanolamine conversion was rate 86%, and the selectivity for ethylenimine was 92%.

EXAMPLE 4

The process in Example 4 was the same as that in Example 1, with exception that the metal ions were loaded in the amount of 10.0% of the mass of the carrier. The solution of the soluble metal salts was prepared in the molar ratio of magnesium ion to iron ion to cesium ion of 5:1:0.1. After the resulting catalyst carrier was immersed in the solution for 8 hours, it was taken out and dried, then roasted in the air at 650° C. to give the catalyst. Isopropanolamine was used as the raw material, and the catalytic reaction conditions and the analysis conditions were the same as that in Example 1. The isopropanolamine conversion rate was 52%, and the selectivity to 2-methyl ethylenimine was 86%.

EXAMPLE 5

The process in Example 5 was the same as that in Example 2, with exception that the metal ions were loaded in the amount of 8.5% of the mass of the carrier. The solution of the soluble metal salts was prepared in the molar ratio of magnesium ion to iron ion to cesium ion of 3:1:0.1. After the resulting catalyst carrier was immersed in the solution for 8 hours, it was taken out and dried, then roasted in the air at 650° C. to give the catalyst. 3-amino-1,2-propanediol was used as the raw material, and the reaction temperature was 385° C. The catalytic reaction conditions and the analysis conditions were the same as that in Example 1. The 3-amino-1,2-propanediol conversion rate was 53.2%, the selectivity for 3-hydroxy-1-azetidine was 53.2%, the selectivity for 2-hydroxymethyl ethylenimine was 24.7%, the selectivity for 3-amino epoxy propane was 9.1%, and the selectivity for others was 13.0%.

EXAMPLE 6

The process in Example 6 was the same as that in Example 3, with exception that 2-amino-2-methyl-1-propanol was used as the raw material, and the reaction temperature was 379° C. The catalytic reaction conditions and the analysis conditions were the same as those in Example 1. The 2-amino-2-methyl-1-propanol conversion rate was 47%, and the selectivity for 2,2-dimethyl ethylenimine was 87.5%.

What is claimed is:
1. A catalyst for synthesizing ethylenimine, characterized in that, the catalyst comprises a carrier and metal ions loaded on the carrier; the carrier is a composite oxide comprising titanium, silicon and phosphorus elements; the metal ions are magnesium ion, iron ion and cesium ion; the molar ratio of the magnesium ion to the iron ion to the cesium ion is (1-10):1:0.1; and the total mass of all the metal ions is 0.5%-10% of that of the carrier.

2. The catalyst for synthesizing ethylenimine of claim 1, characterized in that, the catalyst is prepared by a method comprising:
   (1) mixing silicon oxide, titanium oxide, and an ammonium phosphate salt in an amount of the weight ratio of 5-20:80:15-5 in the oxides form of $SiO_2$ to $TiO_2$ to $P_2O_5$; adding a binder thereto, then kneading and extruding the resulting mixture; drying the extruded mixture, then roasting the dried mixture at a temperature in a range of 600-900° C., thereby obtaining the composite oxide comprising titanium, silicon and phosphorus elements;
   the ammonium phosphate salt is ammonium phosphate, diammonium phosphate, or ammonium dihydrogen phosphate;
   the binder is silica sol or pseudo-boehmite; and
   (2) carrying out fluoridation by reacting the resulting composite oxide in the step (1) with hydrogen fluoride in the absence of oxygen at a temperature in a range of 100-200° C. to give the catalyst carrier.

3. The catalyst for synthesizing ethylenimine of claim 2, characterized in that, the binder is used in an amount of 10%-30% of the mass of the titanium oxide.

4. The catalyst for synthesizing ethylenimine of claim 2, characterized in that, the method for the preparation of the catalyst comprises:
   roasting a catalyst precursor at a temperature in a range of 350-650° C. to give the catalyst; the catalyst precursor is a mixture of the carrier, a soluble salt of magnesium, a soluble salt of iron and a soluble salt of cesium.

5. A method for the synthesis of ethylenimine which comprises treating an amino alcohol in the presence of the catalyst of claim 1 under suitable conditions so as to synthesize ethylenimine.

6. A method for the synthesis of ethylenimine which comprises treating an amino alcohol in the presence of the catalyst of claim 2 under suitable conditions so as to synthesize ethylenimine.

7. A method for the synthesis of ethylenimine which comprises treating an amino alcohol in the presence of the catalyst of claim 3 under suitable conditions so as to synthesize ethylenimine.

8. A method for the synthesis of ethylenimine which comprises treating an amino alcohol in the presence of the catalyst of claim 4 under suitable conditions so as to synthesize ethylenimine.

9. The method of claim 5, characterized in that the suitable conditions comprise a temperature in a range of 370-385° C.

10. The method of claim 6, characterized in that the suitable conditions comprise a temperature in a range of 370-385° C.

11. The method of claim 7, characterized in that the suitable conditions comprise a temperature in a range of 370-385° C.

12. The method of claim 8, characterized in that the suitable conditions comprise a temperature in a range of 370-385° C.

* * * * *